United States Patent [19]

Chao et al.

[11] Patent Number: 5,019,667

[45] Date of Patent: May 28, 1991

[54] PROCESS FOR PURIFICATION OF HYDROCARBONS

[75] Inventors: Chien C. Chao, Millwood, N.Y.; Henry Rastelli, New Fairfield, Conn.

[73] Assignee: UOP, Des Plaines, Ill.

[21] Appl. No.: 509,651

[22] Filed: Apr. 16, 1990

Related U.S. Application Data

[63] Continuation-in-part of Ser. No. 206,280, Jun. 14, 1988, Pat. No. 4,935,580.

[51] Int. Cl.$^5$ .................. B01D 53/04; C07C 7/13; C01C 1/12
[52] U.S. Cl. ............................ 585/820; 585/831; 423/237
[58] Field of Search .............. 585/820, 831; 423/237, 423/239; 55/68, 75

[56] References Cited

U.S. PATENT DOCUMENTS 4,793,837 12/1988 Pontius .................................. 502/60
4,935,580 6/1990 Chao et al. ........................ 585/820

FOREIGN PATENT DOCUMENTS 848501318 1/1985 European Pat. Off. .
61-255994 11/1986 Japan .
62-132542 6/1987 Japan .

OTHER PUBLICATIONS

T. C. Frankiewicz and R. G. Donnelly, Methane/Nitrogen Separation Over the Zeolite Clinoptilolite by Selective Adsorption of Nitrogen, Chapter 11, *Industrial Gas Separation,* American Chemical Society (1983).

*Primary Examiner*—Anthony McFarlane
*Attorney, Agent, or Firm*—Thomas K. McBride; John G. Tolomei

[57] ABSTRACT

Clinoptilolites, including both natural and synthetic clinopilolites which have been ion-exchanged with metal cations such as lithium, sodium, potassium, calcium, magnesium, barium, strontium, zinc, copper, cobalt, iron and manganese, are useful for the removal of traces of ammonia from streams of hydrocarbons having kinetic diameters of not more than about 5Å. The purified hydrocarbons are useful for producing polyolefins.

18 Claims, No Drawings

PROCESS FOR PURIFICATION OF HYDROCARBONS

CROSS-REFERENCE TO RELATED APPLICATION

The present application is a continuation-in-part of U.S. Ser. No. 206,280, filed June 14, 1988, now U.S. Pat. No. 4,935,580.

FIELD OF THE INVENTION

This invention relates to processes for the purification of hydrocarbons. More specifically, this invention relates to processes for the removal of ammonia from hydrocarbons using clinoptilolites. The clinoptilolites may be natural or synthetic clinoptilolites which have been modified by ion-exchange with one or more of a number of metal cations.

BACKGROUND OF THE INVENTION

It is known that processes exist for separating feedstreams containing molecules having differing sizes and shapes by contacting the feedstream with a molecular sieve into which one component of the feedstream to be separated is more strongly adsorbed by the molecular sieve than the other. The more strongly adsorbed component is preferentially adsorbed by the molecular sieve to provide a first product stream which is enriched in the weakly or non-adsorbed component as compared with the feedstream. After the molecular sieve is loaded to a desired extent with the adsorbed component, the conditions of the molecular sieve are varied, e.g., typically either the temperature of or the pressure upon the molecular sieve is altered, so that the adsorbed component can be desorbed, thereby producing a second product stream which is enriched in the adsorbed component as compared with the feedstream.

Important factors in such processes include the capacity of the molecular sieve for the more strongly adsorbable components and the selectivity of the molecular sieve (i.e., the ratio in which the components to be separated are adsorbed). In many such processes, zeolites are the preferred adsorbents because of their high adsorption capacity and, when chosen so that their pores are of an appropriate size, their high selectivity.

Often the zeolites used in the separation of gaseous mixtures are synthetic zeolites. Although natural zeolites are readily available at low cost, natural zeolites are often not favored as adsorbents because it has been felt that the natural zeolites are not sufficiently consistent in composition to be useful as adsorbents in such processes. However, there are relatively few synthetic zeolites with pore sizes in the range of about 3 to 4 Å, which is the pore size range of interest for a number of gaseous separations.

One such separation is the separation of ammonia from methane and other hydrocarbons, including ethylene and propylene, having kinetic diameters not greater than about 5 Å. In the manufacture of polyethylene, ethylene-containing streams which contain ethylene, ethane and propane, together with traces (typically of the order of 10 parts per million or less) of ammonia, often must be purified to reduce the already small proportion of ammonia further before the ethylene stream reaches the polymerization reactor, because the presence of even a few parts per million of ammonia can poison commercial ethylene polymerization catalysts. The ammonia removal can be effected by passing the ethylene stream through a bed of calcium zeolite A. Although calcium A zeolite is an efficient adsorber of ammonia, it also adsorbs relatively large quantities of ethylene, and given the much greater partial pressure of ethylene in the ethylene stream, the quantity of ethylene adsorbed is much greater than that of ammonia. Thus, relatively large quantities of ethylene are wasted in the removal of the traces of ammonia. Similar problems are encountered in the propylene stream used to manufacture polypropylene.

Clinoptilolites are a well-known class of natural zeolites which have occasionally been proposed for the separation of gaseous mixtures, usually light gases such as hydrogen, nitrogen, oxygen, argon, methane, etc.

For example, European Patent Application No. 84850131.8 (Publication No. 132 239) describes a process for the separation of oxygen and argon using as the adsorbent raw clinoptilolite, i.e., clinoptilolite which has not been subjected to any ion-exchange.

The separation of gaseous mixtures of methane and nitrogen using both raw clinoptilolite and clinoptilolite which had been ion-exchanged with calcium cations is described in the following publication; T. C. Frankiewicz and R. G. Donnelly, METHANE/NITROGEN SEPARATION OVER THE ZEOLITE CLINOPTILOLITE BY SELECTIVE ADSORPTION OF NITROGEN, Chapter 11, INDUSTRIAL GAS SEPARATION, American Chemical Society, 1983. They disclose that at long adsorption times, adsorption approaches thermodynamic equilibrium and there is a tendency for adsorbed nitrogen to be replaced by methane. However, since methane diffusion is slower than nitrogen diffusion into clinoptilolite, the separation can be made on a rate basis.

Japanese Patent Application (Kokai) No. 61-255,944 discloses a process for producing a high-caloric gas comprising two adsorption zones wherein nitrogen and other non-combustible low-caloric components are removed from a feed gas, e.g., coke oven gas or methane reaction gas, which also contains hydrogen, methane and other hydrocarbons. This Japanese patent application discloses that the nitrogen is adsorbed on a clinoptilolite adsorbent that may be naturally produced clinoptilolite, natural clinoptilolite that has been crushed as required either in its original form or after ion exchange or other chemical treatment, natural clinoptilolite that has been combined with a suitable binder, then compacted and sintered, natural clinoptilolite that has merely been heat-treated, or from clinoptilolite obtained by a synthetic process. This Japanese patent application does not, however, disclose any specific cations that would be suitable as ion-exchange agents in clinoptilolite for adsorbing ammonia.

Japanese Patent Application (Kokai) No. 62-132,542 discloses an adsorbing and separating composition composed of a clinoptilolite type zeolite containing calcium cations in a mole ratio of $CaO/Al_2O_3$ of 0.4 to 0.75. The application discloses that the composition is useful for separating molecules with a kinetic diameter of less than 3.7 Å from molecules with that of 3.7 Ås or greater, e.g., removal of a small quantity of nitrogen from methane gas, or bulk separation of nitrogen from a methane-containing coke oven gas or coal mine draught gas, etc. There is no specific disclosure or suggestion that this adsorbent would be suitable for separating ammonia from feedstreams containing hydrocarbons.

Accordingly, processes are sought which can separate ammonia from hydrocarbons having kinetic diameters of less than about 5 Å, e.g., methane, ethane, ethylene, propane and propylene, by adsorption using modified clinoptilolite adsorbents. Moreover, processes for the production of the modified clinoptilolite adsorbents are sought.

SUMMARY OF THE INVENTION

By the present invention, processes are provided for the separation of ammonia from hydrocarbon feedstreams containing ammonia and hydrocarbons having kinetic diameters of less than 5 Å. The separation is achieved by using a clinoptilolite molecular sieve that has been ion-exchanged with at least one of lithium, sodium, potassium, calcium, barium, strontium, zinc, copper, cobalt, iron and manganese. Preferably, the clinoptilolite adsorbent is ion-exchanged to an extent such that at least about 60% of the total cations in the clinoptilolite are occupied by sodium cations. The purified hydrocarbons are preferably used to produce polyolefins.

One aspect of the present invention provides a process for separating a minor proportion of ammonia from a hydrocarbon having a kinetic diameter of not more than about 5 Å, which process comprises contacting a feedstream comprising ammonia and the hydrocarbon with a clinoptilolite that has been subjected to ion-exchange with at least one metal cation of the group consisting of lithium, sodium, potassium, calcium, magnesium, barium, strontium, zinc, copper, cobalt, iron and manganese cations to an extent sufficient to cause the ammonia to be selectively adsorbed into the clinoptilolite and withdrawing a product stream at least partially depleted in ammonia relative to the feedstream.

Another aspect of the present invention provides a cyclic adsorption process for separating ammonia from hydrocarbons having a kinetic diameter of less than about 5 Å. The process includes the steps of (a) passing a feedstream containing ammonia and the hydrocarbon to an adsorber bed containing a clinoptilolite molecular sieve that has been subjected to ion-exchange with at least one metal cation selected from lithium, sodium, potassium, calcium, magnesium, barium and strontium cations, at conditions effective to cause the ammonia to be selectively adsorbed on the clinoptilolite, wherein the conditions are selected from a temperature of from about $-50°$ to $100°$ C. and a pressure of from about 0.2 to 1500 psia and withdrawing an effluent stream having a reduced amount of ammonia relative to the feedstream, and; (b) regenerating the adsorber bed by desorbing ammonia therefrom by passing a purge gas having a temperature higher than the adsorption temperature and at least about $50°$ C. therethrough.

Still another aspect of the present invention provides a process for the production of a modified clinoptilolite wherein at least about 40% of the ion-exchangeable cations in the clinoptilolite comprise any one or more of lithium, potassium, calcium, magnesium, barium, strontium, zinc, copper, cobalt, iron and manganese cations. The process comprises subjecting a clinoptilolite to ion-exchange with a solution containing sodium cations until at least about 40% of the ion-exchangeable non-sodium cations in the clinoptilolite have been replaced by sodium cations, thereby producing a sodium clinoptilolite, and thereafter subjecting said sodium clinoptilolite to ion-exchange with a solution containing any one or more of lithium, potassium, calcium, magnesium, barium, strontium, zinc, copper, cobalt, iron and manganese cations.

DETAILED DESCRIPTION OF THE INVENTION

It is well known that the adsorption properties of many zeolites, and hence their ability to separate gaseous mixtures, can be varied by incorporating various metal cations into the zeolites, typically by ion-exchange or impregnation. For example, U.S. Pat. No. 2,882,243 to Milton describes the use of zeolite A having a silica/alumina ratio of $1.85\pm0.5$ and containing hydrogen, ammonium, alkali metal, alkaline earth metal or transition metal cations. The patent states that potassium A zeolite adsorbs water (approximately 3 Å) and excludes hydrocarbons and alcohols, while calcium A zeolite adsorbs straight-chain hydrocarbons (approximately 5 Å) but excludes branched-chain and aromatic hydrocarbons.

Thus, potassium A is commonly referred to as having an effective pore diameter of 3 Å and calcium A similarly is referred to as having an effective pore diameter of 5 Å. The term "effective pore diameter" is used in order to functionally define the pore size of a molecular sieve in terms of what molecules it can adsorb rather than actual dimensions which are often irregular and non-circular, e.g. elliptical. D. W. Breck, in Zeolite Molecular Sieves, John Wiley and Sons (1974), hereby incorporated by reference, describes effective pore diameters at pages 633 to 641.

In most cases, the changes in the adsorption properties of zeolites following ion-exchange are consistent with a physical blocking of the pore opening by the cation introduced; in general, in any given zeolite, the larger the radius of the ion introduced, the smaller the effective pore diameter of the treated zeolite (for example, the pore diameter of potassium A zeolite is smaller than that of calcium A zeolite), as measured by the size of the molecules which can be adsorbed into the zeolite.

Such is not the case, however, with clinoptilolites which demonstrate an unpredictable relationship that is not a simple function of the ionic radii of the cation introduced, i.e., pore blocking. For example, applicants have found that unlike the above-described calcium and potassium ion-exchanged forms of zeolite A, clinoptilolite produces the opposite effect with these two cations. That is, potassium cations, which are larger than calcium cations, provide a clinoptilolite having a larger effective pore diameter than calcium ion-exchanged clinoptilolite. In fact, applicants have found that a calcium ion-exchanged clinoptilolite with a calcium content equivalent to 90% of its ion-exchange capacity defined by its aluminum content essentially excludes both nitrogen and methane. On the other hand, a potassium ion-exchanged clinoptilolite with a potassium content equivalent to 95% of its ion-exchange capacity adsorbs both nitrogen and methane rapidly. Here, the clinoptilolite containing the cation with the larger ionic radii, i.e., potassium, has a larger pore than the clinoptilolite containing the cation with the smaller ionic radii, i.e., calcium.

As already mentioned, the present invention provides processes for separating a minor proportion of ammonia from a hydrocarbon having a kinetic diameter of not more than about 5 Å, which process comprises contacting the ammonia-containing hydrocarbon with a clinoptilolite. As used herein, the term "kinetic diameter" denotes the intermolecular distance of closest approach for two molecules colliding with zero kinetic energy. This definition is well known in the art and more fully elaborated on in the publication; L. Pauling, *Nature of the Chemical Bond*, 3d Ed., Carnell University Press, (1960).

The clinoptilolites used in the process of the present invention may be natural or synthetic clinoptilolites. Synthetic clinoptilolites are not easily synthesized, as noted in *Zeolite Molecular Sieves*, supra at pg 260, and accordingly natural clinoptilolites are preferred. However natural clinoptilolites are variable in composition and chemical analysis shows that the cations in clinoptilolite samples from various mines vary widely. Moreover, natural clinoptilolites frequently contain substantial amounts of impurities, especially soluble silicates, which may cause difficulties in the aggregation or pelletization of the clinoptilolite (discussed in more detail below), or may cause undesirable side-effects which would inhibit practicing the present invention.

In accordance with the present invention, it is required that the clinoptilolites be modified by ion-exchange with at least one metal cation in order to establish the appropriate pore size to perform the separation and to establish compositional uniformity. Among the cations which can usefully be ion-exchanged into clinoptilolites are lithium, sodium, potassium, magnesium, calcium, strontium, barium, zinc, copper, cobalt, iron and manganese cations. Thus, any cation which has the desired effect on pore size can be used for ion-exchange. Moreover, the choice of a particular cation can be dependent on the characteristics of the starting material. Desirably, the ion-exchange is continued until at least about 40% of the cations in the natural clinoptilolite have been replaced by one or more of these cations. The preferred metal cations for treatment of the clinoptilolites used in the process of the present invention are lithium, sodium, calcium, magnesium, barium and strontium cations, with sodium being especially preferred. When sodium is used as the ion-exchange metal cation, it is preferred that the ion-exchange be continued until at least about 60% of the total cations in the clinoptilolite are replaced by sodium cations.

It should be noted that the ion-exchanging can be done in two or more steps. For example, ion-exchanging can be employed to provide a compositionally uniform starting material that is suitable for additional ion-exchanging for pore size tailoring. Thus, additional ion-exchanging can be employed in order to compensate for inherent differences in the naturally occurring raw material thereby enhancing the performance for separating ammonia from hydrocarbons. For example, despite the unpredictability of ion-exchanging clinoptilolite, Applicants have determined that the effective pore diameter of the clinoptilolite molecular sieves can be increased by ion-exchanging with potassium, strontium, or barium cations, with potassium being a preferred cation for this purpose. On the other hand, the effective pore diameter of the clinoptilolite can be decreased by ion-exchanging with calcium, sodium, or lithium cations.

Since clinoptilolite is a natural material, the particle sizes of the commercial product varies, and the particle size of the clinoptilolite may affect the speed and completeness of the ion-exchange reaction. In general, it is recommended that the particle size of the clinoptilolite used in the ion-exchange reaction be not greater than about 8 U.S. mesh. Although the particle sizes of many commercial clinoptilolites are greater, their particle sizes are readily reduced by grinding or other techniques which will be familiar to those skilled in the ion-exchange of molecular sieves.

Techniques for the ion-exchange of zeolites such as clinoptilolite are well-known to those skilled in the molecular sieve art, and hence will not be described in detail herein. In the ion-exchange, the cation is conveniently present in the solution in the form of its chloride. It is desirable that the ion-exchange be continued until at least about 40%, and preferably at least about 60%, of the cations in the original clinoptilolite have been replaced, and in most cases it is convenient to continue the ion-exchange until no further amount of the desired cation can easily be introduced into the clinoptilolite. To secure maximum replacement of the original clinoptilolite cations, it is recommended that the ion-exchange be conducted using a solution containing a quantity of the cation to be introduced which is from about 2 to about 100 times the ion-exchange capacity of the clinoptilolite. Typically, the ion-exchange solution will contain from about 0.1 to about 5 moles per liter of the cation, and will be contacted with the original clinoptilolite for at least about 1 hour. The ion-exchange may be conducted at ambient temperature, although in many cases carrying out the ion-exchange at elevated temperatures, usually less than 100° C., accelerates the ion-exchange process.

Since clinoptilolite is a natural material of variable composition, the cations present in the raw clinoptilolite vary, although typically the cations include a major proportion of alkali metals. It is typically found that, even after the most exhaustive ion-exchange, a proportion of the original clinoptilolite cations, i.e., from about 5 to 15 wt. % cannot be replaced by other cations. However, the presence of this small proportion of the original clinoptilolite cations does not interfere with the use of the ion-exchanged clinoptilolites in the process of the present invention.

As noted above, any of the modified clinoptilolites of the present invention can be prepared directly by ion-exchange of natural clinoptilolite with the appropriate cation. However, in practice such direct ion-exchange may not be the most economical or practical technique. Being natural minerals, clinoptilolites are variable in composition and frequently contain substantial amounts of impurities, especially soluble silicates. To ensure as complete an ion-exchange as possible, and also to remove impurities, it is desirable to effect the ion-exchange of the clinoptilolite using a large excess of the cation which it is desired to introduce. However, if, for example, a large excess of barium is used in such an ion-exchange, the disposal and/or recovery of barium from the used ion-exchange solution presents a difficult environmental problem, in view of the limitations on release of poisonous barium salts into the environment. Furthermore, some impurities, including some silicates, which are removed in a sodium ion-exchange are not removed in a barium ion-exchange because the relevant barium compounds are much less soluble than their sodium counterparts.

When the clinoptilolites of the present invention are to be used in industrial adsorbers, it may be preferred to aggregate (pelletize) the modified clinoptilolite to control the macropore diffusion, or else in an industrial size adsorption column pulverulent clinoptilolite may compact, thereby blocking, or at least significantly reducing flow through, the column. Those skilled in molecular sieve technology are aware of conventional techniques for aggregating molecular sieves; such techniques usually involve mixing the molecular sieve with a binder, which is typically a clay, forming the mixture into an aggregate, typically by extrusion or bead formation, and heating the formed molecular sieve/clay mixture to a temperature of about 600°-700° C. to convert the green aggregate into one which is resistant to crushing.

The binders used to aggregate the clinoptilolites may include clays, silicas, aluminas, metal oxides and mixtures thereof. In addition, the clinoptilolites may be formed with materials such as silica, alumina, silica-alumina, silica-magnesia, silica-zirconia, silica-thoria, silica-berylia, and silica-titania, as well as ternary compositions, such as silica-alumina-thoria, silica-alumina-zirconia and clays present as binders. The relative proportions of the above materials and the clinoptilolites may vary widely with the clinoptilolite content ranging between about 1 and about 99, preferably between about 60 to 95, percent by weight of the composite. Where the clinoptilolite is to be formed into aggregates prior to use, such aggregates are desirably about 1 to about 4 mm. in diameter.

To avoid the aforementioned difficulties, it is generally preferred to produce modified clinoptilolites of the present invention other than sodium clinoptilolite by first subjecting raw clinoptilolite to a sodium ion-exchange, aggregating the sodium clinoptilolite thus produced, and then effecting a second ion-exchange on the aggregated material to introduce the desired non-sodium cations. When a sodium clinoptilolite itself is to be used, it is in general not necessary to carry out a second sodium ion-exchange after aggregation; the aggregated sodium clinoptilolite may be used without further processing and gives satisfactory results, which do not appear to be significantly improved by a second ion-exchange.

Before being used in the processes of the present invention, the clinoptilolites need to be activated by calcining, i.e., heating. If the clinoptilolite is aggregated as discussed above, the heat required for aggregation will normally be sufficient to effect activation also, so that no further heating is required. If, however, the clinoptilolite is not to be aggregated, a separate activation step will usually be required. Moreover, if the ore is used directly or ion-exchange is conducted after the aggregation, a separated activation step usually will be required. Clinoptilolites can be activated by heating in air, inert atmosphere, or vacuum to a temperature and for a time sufficient to cause the clinoptilolite to become activated. The term "activated" is used herein to describe an adsorbent having a reduced water content relative to being in equilibrium with atmospheric air. Typical activation conditions include a temperature of 350°-700° C. and a time of 30 minutes to 20 hours which is sufficient to reduce the water content of clinoptilolite to about 0.2 to 2 wt. %. Preferably the clinoptilolites are activated by heating in an air or nitrogen purge stream or in vacuum at approximately 300°-650° C. for about 1 hour. The temperature needed for activation of any particular specimen of clinoptilolite can be easily determined by routine empirical tests where typical adsorption properties such as absolute loadings or adsorption rates are measured for samples activated at various temperatures.

Although ion-exchange of clinoptilolite does produce a modified clinoptilolite having a consistent pore size, the exact pore size depends not only upon the metal cation(s) exchanged but also upon the thermal treatment of the product following ion-exchange. In general, there is a tendency for the pore size of the modified clinoptilolites of this invention to decrease with exposure to increasing temperature. Accordingly, in selecting an activation temperature for the modified clinoptilolites, care should be taken not to heat modified clinoptilolites to temperatures for which cause reductions in pore size so severe as to adversely affect the performance of the modified clinoptilolite in the process of the present invention, i.e., higher than 700° C. Although the behavior of the modified clinoptilolites on exposure to heat does limit the activation temperatures which can be employed, the thermal reduction in pore size does offer the possibility of "fine tuning" the pore size of a modified clinoptilolite to optimize its performance in the process of the present invention.

The process of the present invention is primarily intended for removal of traces of ammonia from hydrocarbons, especially ethylene streams (comprising mainly ethylene and ethane) such as those used in the production of polyethylene (and the corresponding propylene streams, comprising mainly propylene and propane, such as those used in the manufacture of polypropylene), where the presence of even a few parts per million of ammonia can be undesirable. Thus, in one aspect of the invention, the purified hydrocarbons are polymerized to form polyolefins, preferably ethylene. In such streams, the ammonia content of the gas is normally not greater than about 200 parts per million, and the ammonia partial pressure not greater than about 20 Torr. As already mentioned, sodium clinoptilolite is the preferred material for this process. The clinoptilolites of the process of the present invention can also remove water as well as carbon dioxide which may also be present in the hydrocarbon stream in amounts similar to that for ammonia. The details of the polymerization process itself are known in the art and need not be further disclosed herein.

The present process may also be useful for the separation of ammonia from methane or other hydrocarbons. The present invention may also be used to separate ammonia from butanes and butenes, or even larger hydrocarbons (for example n-hexane) which have kinetic diameters not greater than about 5 Å.

Since these types of processes involve the separation of minor amounts of ammonia from much larger amounts of hydrocarbons, they may be effected in the conventional manner by simply passing the hydrocarbon stream through a bed of the clinoptilolite, which is normally in aggregate form during an adsorption step. As the adsorption step continues, there develops in the bed a so-called "front" between the clinoptilolite loaded with ammonia and clinoptilolite not so loaded, and this front moves through the bed in the direction of gas flow. Preferably, the temperature during the adsorption step is maintained between about −15° to +65° C. Before the front reaches the downstream end of the bed (which would allow impure hydrocarbon gas to leave the bed), the bed is preferably regenerated by cutting off the flow of hydrocarbon gas and passing through the bed a purge gas which causes desorption of the ammonia (and water, if any is present) from the bed. In industrial practice, the purge gas is typically nitrogen or natural gas heated to a temperature in the range of 50° to 350° C., and such a purge gas is also satisfactory in the processes of the present invention. It is also important to note that other adsorption cycles such as pressure swing or purge cycles can be employed. Such cycles form no critical part of the present invention, are well known to those skilled in the art, and accordingly, will not be further discussed herein.

The following Examples are given, though by way of illustration only, to show preferred processes of the present invention. All adsorption measurements are at 23° C. unless otherwise stated. Furthermore, all separation factors given in the form "Separation factor X/Y"

are calculated by

Separation factor $X/Y = P_y L_x / P_x L_y$ where $P_x$ and $P_y$ are the pressures of components X and Y respectively and $L_x$ and $L_y$ are the corresponding loadings of X and Y in millimoles per gram of adsorbent.

EXAMPLES

Example 1: Natural Clinoptilolites

Seven different samples of commercially-available clinoptilolites were used in these experiments and as starting materials for the preparation of some of the modified clinoptilolites prepared in the later Examples. The chemical analyses of these clinoptilolites are shown in Table 1 below, while ammonia and ethylene separation data are shown in Table 2. For comparison, Table 2 includes data for zeolite 5A, a commercial material used for gas separations.

TABLE 1

| Component (wt. %) | Clinoptilolite | | | | | | |
|---|---|---|---|---|---|---|---|
| | A | B | C | D | E | F | G |
| Loss on ignition | 12.6 | 15.2 | 13.2 | 11.6 | 13.6 | 13.8 | 13.3 |
| $Al_2O_3$ (anhydrous) | 14.188 | 12.618 | 12.903 | 12.670 | 13.426 | 13.573 | 13.379 |
| $SiO_2$ (anhydrous) | 72.883 | 75.236 | 76.152 | 75.924 | 75.964 | 74.710 | 75.779 |
| $Na_2O$ (anhydrous) | 3.547 | 2.252 | 4.090 | 3.801 | 3.831 | 3.840 | 3.656 |
| $K_2O$ (anhydrous) | 1.796 | 2.170 | 4.078 | 4.355 | 2.280 | 2.541 | 1.984 |
| MgO (anhydrous) | 1.796 | 2.123 | 0.325 | 0.575 | 0.714 | 1.044 | 0.734 |
| CaO (anhydrous) | 3.341 | 2.724 | 1.039 | 1.403 | 1.887 | 2.390 | 2.434 |
| SrO (anhydrous) | 0.049 | 0.018 | — | 0.032 | 0.345 | 0.563 | 0.406 |
| BaO (anhydrous) | 0.135 | 0.051 | — | 0.376 | 0.071 | 0.246 | 0.248 |
| $Fe_2O_3$ (anhydrous) | 2.208 | 3.054 | 0.919 | 0.989 | 1.262 | 1.508 | 1.292 |

TABLE 2

| Adsorption (wt. %) | Clinoptilolite | | | | | | | |
|---|---|---|---|---|---|---|---|---|
| | A | B | C | D | E | F | G | 5A |
| $NH_3$, 1 Torr 3 hours | 3.9 | 4.6 | 3.2 | 2.3 | 3.6 | 1.3 | 2.6 | 4.8 |
| $C_2H_4$ 700 Torr 3 hours | 0.981 | 2.177 | 0.990 | 0.904 | 1.453 | 1.098 | 2.222 | 7.700 |
| Separation factor $NH_3/C_2H_4$ | 2486 | 1464 | 2263 | 1789 | 1738 | 829 | 820 | 436 |

From the data in Table 2, it will be seen that all the seven clinoptilolite specimens had ammonia/ethylene separation factors substantially better than that of zeolite 5A.

Example 2: Sodium Clinoptilolite

1500 Gm. (dry weight) of clinoptilolite C in Example 1 was ground to 30×50 U.S. mesh and placed in a jacketed glass column. The column was heated to 80° C. by passing oil through the jacket, and 30 liters of 1.86N sodium chloride solution was passed through the column at a flow rate of 19 ml/minute for 16 hours. The clinoptilolite was then washed by passing distilled water through the column, and dried in air at ambient temperature.

The sodium clinoptilolite thus produced was subjected to chemical analysis and its adsorption properties were measured using a McBain quartz spring balance. Before being used in the adsorption tests, the sodium clinoptilolite was activated by heating to 375° C. under vacuum for one hour.

Part of the sodium clinoptilolite was then subjected to a second sodium ion-exchange. 200 grams of the sodium clinoptilolite were treated in the same column as before by passing 9 liters of 0.5M sodium chloride solution over the clinoptilolite for 16 hours. The chemical analysis and adsorption properties of the doubly-exchanged sodium clinoptilolite were then measured in the same manner as before.

The chemical analyses of both sodium clinoptilolites are shown in Table 3 below, and their adsorption properties are shown in Table 4, along with those of 5A zeolite; in both cases, the singly-exchanged material is designated "NaClino", while the doubly-exchanged material is designated "NaNaClino". For comparative purposes, the chemical analysis and adsorption data for the clinoptilolite C starting material (given in Tables 1 and 2 above) are repeated in Tables 3 and 4.

TABLE 3

| Component (wt. %) | NaClino | NaNaClino | Clino C |
|---|---|---|---|
| Loss on ignition | 13.3 | 14.5 | 13.2 |
| $Al_2O_3$ (anhydrous) | 13.033 | 12.982 | 12.903 |
| $SiO_2$ (anhydrous) | 79.123 | 78.246 | 76.152 |
| $Na_2O$ (anhydrous) | 6.332 | 6.199 | 4.090 |
| $K_2O$ (anhydrous) | 1.465 | 0.750 | 4.078 |
| MgO (anhydrous) | 0.219 | — | 0.325 |
| CaO (anhydrous) | 0.276 | 0.199 | 1.039 |
| $Fe_2O_3$ (anhydrous) | 0.980 | — | 0.919 |

TABLE 4

| Adsorption (wt. %) | NaClino | NaNaClino | Clino C | 5A |
|---|---|---|---|---|
| $NH_3$, 1 Torr 3 hours | 2.8 | 3.0 | 3.2 | 4.8 |
| $CH_4$, 700 Torr 3 hours | 0.100 | 0.100 | — | — |
| Separation factor $NH_3/CH_4$ | 19600 | 21000 | | |
| Water, 4.7 Torr | — | 5.4 | — | 23.0 |
| Separation factor $H_2O/CH_4$ | — | 17848 | — | — |
| $C_2H_6$, 50 Torr 3 hours | 0.100 | 0.100 | — | 3.1 |
| Separation factor | — | 2390 | | 132 |

TABLE 4-continued

| Adsorption (wt. %) | NaClino | NaNaClino | Clino C | 5A |
|---|---|---|---|---|
| $H_2O/C_2H_6$ Separation factor $NH_3/C_2H_6$ | 1400 | 1500 | — | 77 |
| $C_2H_4$, 50 Torr 3 hours | 0.300 | 0.200 | — | 4.8 |
| Separation factor $H_2O/C_2H_4$, 50 Torr | — | 1116 | — | 165 |
| Separation factor $NH_3/C_2H_4$, 50 Torr | 467 | 750 | — | 50 |
| $C_2H_4$, 700 Torr 3 hours | — | 0.507 | 0.990 | 7.7 |
| Separation factor $H_2O/C_2H_4$, 700 Torr | — | 2374 | — | 692 |
| Separation factor $NH_3/C_2H_4$, 700 Torr | — | 3684 | 2262 | 436 |

From the data in Tables 3 and 4, it will be seen that both the singly and doubly-exchanged sodium clinoptilolites would be useful for the separation of ammonia and water from hydrocarbon gas streams, that both are superior to the untreated clinoptilolite C for this purpose, and that all three of the clinoptilolites are much better than 5A zeolite. The second sodium ion-exchange does not appreciably increase the sodium content of the clinoptilolite, but does reduce the potassium and calcium contents. However, since the second sodium ion-exchange does not appreciably increase the relevant separation factors, in general a single sodium ion-exchange would be sufficient to provide a material suitable for use in the process of the present invention.

Example 3: Potassium C

50 Gm. (dry weight) of the clinoptilolite ore A in Table 1 was placed in a jacketed glass column. The column was heated to 90° C. by passing oil through the jacket, and 30 liters of 0.4N potassium chloride solution was passed through the column at a flow rate of 5 ml/minute for 50 hours. The clinoptilolite was then washed by passing distilled water through the column, and dried in air at ambient temperature.

The potassium clinoptilolite thus produced was subjected to chemical analysis and its adsorption properties were measured using a McBain quartz spring balance. Before being used in the adsorption tests, the potassium clinoptilolite was activated by heating to 375° C. under vacuum for one hour. The results are shown in Tables 5 and 6 below.

TABLE 5

| Component (wt. %) | KClino |
|---|---|
| Loss on ignition | 11.3 |
| $Al_2O_3$ (anhydrous) | 12.63 |
| $SiO_2$ (anhydrous) | 75.86 |
| $Na_2O$ (anhydrous) | 0.14 |
| $K_2O$ (anhydrous) | 11.6 |
| MgO (anhydrous) | — |
| CaO (anhydrous) | 1.36 |

TABLE 6

| Adsorption (wt %) | KClino |
|---|---|
| $NH_3$, 1 Torr 3 hours | 3.3 |
| $CH_4$, 700 Torr 3 hours | 1.33 |
| Separation factor $NH_3/CH_4$ | 1176 |
| $C_2H_6$, 50 Torr 3 hours | 2.65 |
| Separation factor $NH_3/C_2H_6$ | 62 |
| $C_2H_4$, 50 Torr 3 hours | 2.95 |

TABLE 6-continued

| Adsorption (wt %) | KClino |
|---|---|
| Separation factor $NH_3/C_2H_4$ | 56 |

These results indicate that the potassium clinoptilolite was able to separate ammonia from methane and ethane, but that its relevant separation factors were lower than those of the natural clinoptilolite from which it is derived or those of the sodium clinoptilolites prepared in Example 2 above.

These adsorption results also demonstrate that, contrary to what would be expected on the basis of the ionic radii of the cations involved ($Na^+$ has a Pauling ionic radius of 0.95 Å, while $K^+$ has a Pauling ionic radius of 1.33 Å), the potassium clinoptilolite has a substantially greater pore size than the sodium clinoptilolite. Accordingly, the pore size of a modified clinoptilolite of this invention cannot be predicted from a knowledge of the ionic radius of the cation introduced and the normal pore blocking mechanism which is typical of the zeolites, and thus the cation must affect the pore size of the clinoptilolite by some mechanism other than simple physical pore blocking.

Examples 4–9: Adsorption Properties of Various Modified Clinoptilolites

A number of modified clinoptilolites were prepared in substantially the same way as in Example 2 above, and their adsorption properties were determined using the McBain balance, in some cases after pelletization with clay. The methods of preparation are summarized in Table 7 below; in the column headed "Starting Material", "Clino A" etc. refers to the natural clinoptilolites described in Example 1 above, while "NaClino" refers to the singly-exchanged material produced in Example 2 above. A "—" in the column headed "Binder" indicates that the modified clinoptilolite was not pelletized before the adsorption measurements were made. Chemical analyses of the modified clinoptilolites are given in Table 8 and adsorption data in Table 9. All adsorption measurements were taken at 23° C. A prime (') following the Clinoptilolite letter indicates material from the same deposit as the corresponding clinoptilolite in Example 1 above, but from a different lot of ore.

TABLE 7

| Example # | Starting Material | Ion-exchange solution | | Binder | Modifier Material |
|---|---|---|---|---|---|
| 4 | NaClino | 0.4 M LiCl | 100× excess | — | Li—Na |
| 5 | NaClino | 0.25 M $CaCl_2$ | 10× excess | — | Ca—Na |
| 6 | NaClino | 0.25 M $SrCl_2$ | 10× excess | — | Sr—Na |
| 7 | Naclino | 0.20 M $ZnCl_2$ | 100× excess | — | Zn—Na |
| 8 | Clino A' | As Example 2 | | | Na |
| 9 | Clino A' | KCl, | 100× excess | — | K |

TABLE 8

| Component (wt. %) | 4 | 5 | 6 | 7 | 8 | 9 |
|---|---|---|---|---|---|---|
| Loss on ignition | 13.9 | 14.8 | 14.2 | 13.8 | 13.6 | 11.3 |
| $Al_2O_3$ (anhydrous) | 13.473 | 13.263 | 12.354 | 12.529 | 12.847 | 12.627 |
| $SiO_2$ (anhydrous) | 81.185 | 78.286 | 74.476 | 75.638 | 76.968 | 75.862 |
| $Na_2O$ (anhydrous) | 0.269 | 0.263 | 0.350 | 0.309 | 7.141 | 0.135 |
| $K_2O$ | 1.069 | 0.947 | 1.049 | 1.636 | 0.271 | 11.612 |

TABLE 8-continued

| Component (wt. %) | 4 | 5 | 6 | 7 | 8 | 9 |
|---|---|---|---|---|---|---|
| (anhydrous) MgO | 0.228 | 0.224 | — | 0.194 | 0.223 | 0.265 |
| (anhydrous) CaO | 0.497 | 6.573 | 0.350 | 0.527 | 1.458 | 1.364 |
| (anhydrous) BaO | — | — | — | 2.877 | — | — |
| (anhydrous) Fe$_2$O$_3$ | 0.868 | 0.805 | — | 0.765 | 0.949 | 0.964 |
| (anhydrous) Other | 3.287 Li$_2$O | — | 7.226 SrO | 5.487 ZnO | — | — |

TABLE 9

| Adsorption (wt. %) | 4 | 5 | 7 | 8 | 9 |
|---|---|---|---|---|---|
| NH$_3$, 1 Torr 3 hours | 4.3 | 1.1 | 3.6 | 3.1 | 3.3 |
| CH$_4$, 700 Torr 3 hours | 0.42 | 0.09 | 1.56 | 0.30 | 1.33 |
| Separation factor NH$_3$/CH$_4$ | 7166 | 8555 | 1615 | 7233 | 1736 |
| C$_2$H$_6$, 50 Torr 3 hours | 0.48 | 0.10 | 1.76 | 0.46 | 2.65 |
| Separation factor NH$_3$/C$_2$H$_6$ | 448 | 550 | 102 | 337 | 62 |
| C$_2$H$_4$, 50 Torr 3 hours | 0.99 | 0.03 | 2.83 | 1.06 | 2.95 |
| Separation factor NH$_3$/C$_2$H$_4$ | 217 | 1833 | 63.6 | 146 | 55.9 |

The above data show that the modified clinoptilolites strongly adsorb NH$_3$ but have low adsorptions of methane, ethylene and ethane, so that these clinoptilolites are useful for separating ammonia from hydrocarbon streams. The potassium and zinc clinoptilolites are comparable to zeolite 5A in their ability to effect these separations (see the data for zeolite 5A in Table 4 above), while the other modified clinoptilolites have separation factors much better than zeolite 5A, and should thus provide better selectivity for the separation of ammonia from methane, ethane, and ethylene. More specifically, Li-Na exchanged clino (Example 4), Zn-Na exchanged clino (Example 7), Na exchanged clino (Example 8) and K exchanged clino (Example 9) all had high loading capacities for NH$_3$, i.e., above 3 wt. %. Furthermore, the Li-Na exchanged clino (Example 4), Ca-Na exchanged clino (Example 5), and Na exchanged clino (Example 8) had high separation factors for NH$_3$ over CH$_4$, C$_2$H$_6$ and C$_2$H$_4$, i.e., at least over 100 for all components. When combining the results of capacity and separation factor, it is seen that Li-Na exchanged clino (Example 4) and Na exchanged clino (Example 8) have both high capacities and separation factors and thus are more preferred. Na exchanged clino (Example 8) is most preferred because it can be prepared by ion-exchanging with a relatively inexpensive solution of sodium cations.

We claim:

1. A process for separating a minor proportion of ammonia from a hydrocarbon having a kinetic diameter of not more than about 5 Å, which process comprises contacting a feedstream comprising ammonia and the hydrocarbon with clinoptilolite that has been subjected to ion-exchange with at least one metal cation of the group consisting of lithium, sodium, potassium, calcium, magnesium, barium and strontium, zinc, copper, cobalt, iron and manganese cations to an extent sufficient to cause the ammonia to be selectively adsorbed into the clinoptilolite and withdrawing a product stream at least partially depleted in ammonia relative to the feedstream.

2. A process according to claim 1 wherein the clinoptilolite is a natural clinoptilolite.

3. A process according to claim 1 wherein the metal cation is at least one of lithium, sodium, calcium, magnesium, barium and strontium cations.

4. A process according to claim 3 wherein the metal cation is sodium.

5. A process according to claim 4 wherein the clinoptilolite is ion-exchanged to the extent that at least about 60% of the total cations in the clinoptilolite are exchanged with sodium cations.

6. A process according to claim 1 wherein said contacting is conducted at a temperature in the range of from −15° to +60° C.

7. A process according to claim 1 wherein the ammonia content of the hydrocarbon is not greater than about 200 parts per million.

8. A process according to claim 1 wherein the partial pressure of ammonia in the feedstream is not greater than about 20 Torr.

9. A process according to claim 1, wherein the hydrocarbon is an acyclic hydrocarbon containing not more than 5 carbon atoms.

10. A process according to claim 9, wherein the hydrocarbon is an acyclic hydrocarbon containing not more than 4 carbon atoms.

11. A process according to claim 10 wherein the hydrocarbon is selected from the group consisting of methane, ethylene, ethane, propylene, propane, a butane and a butene.

12. A process according to claim 11 wherein the hydrocarbon is selected from the group consisting of ethylene, ethane, propylene and propane.

13. A process according to claim 12 wherein the hydrocarbon consists of ethylene.

14. A process according to claim 13 wherein the clinoptilolite is a sodium clinoptilolite.

15. A process according to claim 1 wherein, after ammonia has been adsorbed into the clinoptilolite, a purge gas having a temperature of at least about 50° C. is passed through the clinoptilolite, thereby causing desorption of the ammonia from the clinoptilolite.

16. A process according to claim 15 wherein the inert gas is nitrogen or methane.

17. A cyclic adsorption process for separating ammonia from hydrocarbons having molecules with a kinetic diameter of less than about 5 Å, which process comprises:

(a) passing a feedstream comprising ammonia and the hydrocarbon to an adsorber bed containing a clinoptilolite molecular sieve that has been subjected to ion-exchange with at least one metal cation of the group consisting of lithium, sodium, potassium, calcium, magnesium, barium and strontium cations, at conditions effective to cause the ammonia to be selectively adsorbed on said clinoptilolite, said conditions selected from a temperature of from about −50° to 100° C. and at a pressure of from about 0.2 to 1500 psia and withdrawing an effluent stream having a reduced amount of ammonia relative to the feed stream, and;

(b) regenerating said adsorber bed by desorbing ammonia therefrom by passing an inert gas having a temperature higher than the adsorption temperature and at least about 50° C. therethrough.

18. A process according to claim 17 wherein the inert gas is nitrogen or methane.

* * * * *